United States Patent [19]
Klyosov et al.

[11] Patent Number: 5,919,424
[45] Date of Patent: Jul. 6, 1999

[54] METHOD OF RECOVERING MINERALS FROM PAPERMAKING SLUDGE AND SLUDGE-DERIVED ASH

[75] Inventors: Anatole A. Klyosov, Newton; George P. Philippidis, Boston; Yiannis A. Monovoukas, Walthman, all of Mass.

[73] Assignee: Thermo Fibergen, Inc., Bedford, Mass.

[21] Appl. No.: 08/877,548

[22] Filed: Jun. 17, 1997

[51] Int. Cl.$^6$ ................................................ C01F 11/18
[52] U.S. Cl. ........................................ 423/165; 210/928
[58] Field of Search ................................ 423/155, 162, 423/163, 158, 165; 210/928

[56] References Cited

U.S. PATENT DOCUMENTS

| | | | |
|---|---|---|---|
| 3,812,235 | 5/1974 | Robinson | 423/158 |
| 4,017,391 | 4/1977 | Black | 423/432 |
| 4,100,264 | 7/1978 | Heytmeijer et al. | 423/430 |
| 4,420,369 | 12/1983 | Eaton et al. | 210/928 |
| 5,007,964 | 4/1991 | Tsukisaka et al. | 106/464 |
| 5,122,350 | 6/1992 | Bryan | 423/155 |
| 5,376,343 | 12/1994 | Fouche | 423/165 |

OTHER PUBLICATIONS

Johnston et al., *Appita Journal*, 49(6):397–402 (1996) No Month.

Pera et al., "Paper Mill Sludge: A Source of Valuable Cement Additives," *Paper Recycling '96 Conf.* (1996) No Month.

Sohara, "Recycling Mineral Fillers from Deinking Sludges," *Paper Recycling '96 Conf.* (1996) No Month.

Chattaraj et al., Indian Pulp & Paper, Jun.–Jul. 1981, at 21–28.

*Primary Examiner*—Michael Lewis
*Assistant Examiner*—Stuart L. Hendrickson
*Attorney, Agent, or Firm*—Cesari and McKenna, LLP

[57] ABSTRACT

Extraction of minerals from papermaking sludge or sludge-derived ash is accomplished by mixing with a solution of an inorganic or organic acid—generally 0.1% to 35% by weight, preferably 2% to 20%, and most preferably 3% to 8% by weight. In preferred embodiments, the material is carried as an aqueous solution and combined with 2% to 20%, and most preferably 3% to 6%, HCl; 2% to 25%, and most preferably 8%, $HNO_3$; 2% to 30%, and most preferably 8%, acetic acid. Generally, the amount of acid added into the reaction mixture preferably is 0.8 to 2.0 times the stoichiometric calcium carbonate content in the mixture, more preferably 0.8 to 1.2 times the stoichiometric content, and most preferably matched to the stoichiometric content of calcium carbonate in the mixture. The acid-containing mixture is incubated (with agitation, if desired, to shorten the reaction time) to solubilize the desired minerals, following which the liquid phase is isolated, and mineral salts recovered therefrom.

27 Claims, No Drawings

5,919,424

METHOD OF RECOVERING MINERALS FROM PAPERMAKING SLUDGE AND SLUDGE-DERIVED ASH

FIELD OF THE INVENTION

The present invention relates to utilization of renewable resources and industrial wastes, such as pulp and paper sludge and products of their incineration, and in particular to recovery of minerals from these materials.

BACKGROUND OF THE INVENTION

Pulp and paper sludge (a byproduct of primary pulping operations, recycle streams or waste paper pulping and the like), as well as the products of its incineration, represent an environmental and disposal problem for manufacturers of pulp and paper. Generally, pulp and paper sludge is unsuitable for paper making, although it generally includes the same components—lignin, cellulose, hemicellulose, calcium carbonate, clay, and other inorganic components—as those present in the paper pulp itself.

Paper sludge has traditionally been disposed of by landfilling, composting, utilization by the cement industry, and by incineration. The latter option, in turn, creates another problem, namely, disposal of the resulting ash, which often constitutes up to 50% (and sometimes as much as 80% or higher) of the volume of the sludge itself. Calcium carbonate, in the form of precipitated calcium carbonate (PCC) or ground calcium carbonate (GCC), typically constitutes 20% and up to 75% of dry sludge content. Calcium carbonate is a natural carbonate which is loaded, typically together with clay, into paper as a coating and filler to improve the mechanical characteristics as well as the appearance of paper. Despite their natural abundance, calcium salts are generally expensive products because of the difficulties and expenses of their purification from natural mineral deposits. For instance, paper-quality PCC is typically produced from natural limestone via many stages including the calcination of limestone in an industrial kiln (into either a calcitic or a dolomitic lime), slaking, slurrying, carbonating, and a number of refining steps.

Calcium-derived compounds undergo chemical changes when paper sludge is incinerated. These changes were outlined in recent articles (see Sohara, "Recycling Mineral Fillers from Deinking Sludges," *Paper Recycling '96 Conf.* 1996) (hereafter "Sohara"); Pera et al., "Paper Mill Sludge: A Source of Valuable Cement Additives," *Paper Recycling '96 Conf.* (1996). The organic components of sludge are completely destroyed during incineration. Thermal dehydration of clay results in calcined aluminosilicates, which form complex chemical compounds with decarboxylated calcium carbonate of general formula $Ca_nAl_aSi_bO_c$, that is, calcium aluminosilicates. Silica, which enters the thermally treated sludge from the fluidizing medium (sand) during the incineration process and also as a product of kaolin thermal breakdown, reacts with calcium oxide (derived from thermal decarboxylation of calcium carbonate) forming calcium silicate $CaSiO_3$. Other minerals present in sludges (as pigments, fillers, traces of flocculants, etc.), such as those based on magnesium, potassium, titanium and others, make the composition of the mineral content even more complex. The particular species formed depends mainly upon the relative amount (and nature) of clay in the mineral fraction of the sludge, the amount of calcium carbonate, and the conditions of the thermal treatment.

Formation of calcium silicates in the course of incineration of lime-treated "green liquor" residues, containing calcium carbonate and silica, was described in Chattaraj et al., *Indian Pulp & Paper*, June–July 1981, at 21–28. Such an incineration leads to the formation of di- and tri-calcium silicates (presumably, larnite $Ca_2SiO_4$ and gehlenite $Ca_2Al_2SiO_7$ among them), which in turn form a fine gelatinous precipitate of calcium silicate dihydrate in the caustic liquor ("white liquor"). The authors reported that calcium silicates make calcination of calcium carbonate more difficult. Moreover, calcium silicate particles that are formed as a result of the calcination process are fused into irregularly shaped abrasive agglomerates unsuitable for paper filling and coating; see Johnston et al., *Appita Journal*, 49(6):397–402 (1996).

Unfortunately, the inorganic content of sludge and sludge-derived ash is generally largely or totally wasted. At best, the prior art describes utilization of incineration ash for production of low-end, impure products of limited market value. For example, Sohara details processing of such ash to precipitate calcium carbonate on the surface of the ash itself (without separation from the ash). In particular, an aqueous slurry of incineration ash is carbonated with carbon dioxide gas; calcium carbonate nucleates and grows during the precipitation reaction. The resulting mixture of precipitated calcium carbonate and ash still contains from 10% to 30% incineration ash, and represents an undifferentiated agglomeration of minerals and clay.

Lacking in the prior art is a cost-effective method of producing pure, high-grade calcium and other mineral salts from papermaking sludge or ash derived therefrom.

DESCRIPTION OF THE INVENTION

BRIEF SUMMARY OF THE INVENTION

The invention provides a method of obtaining minerals from papermaking sludge (pressed or dried) or incinerated sludge (ash) notwithstanding the various chemical changes that occur during incineration. The invention involves combination of the pressed or dried sludge or sludge-derived ash with a diluted acid, following which the solid content is separated from the liquid content to obtain a solids-free solution of the calcium salt. The separation of the liquid from the solid residue is preferably carried out using belt presses, screw presses, centrifuges, filters, or a combination. The solids obtained can be further washed with water in order to increase the yield of the calcium salt.

The invention can be practiced using virtually any acid that reacts with solid $CaCO_3$ to produce an aqueous calcium salt. Suitable examples include hydrochloric acid, nitric acid, and acetic acid. In one embodiment of the invention, precipitated $CaCO_3$ is obtained from the solids-free liquid fraction using carbon dioxide gas, as described in U.S. Pat. Nos. 5,007,964 and 5,376,343; or by other means, as described in U.S. Pat. No. 4,100,264. The '964, '343 and '264 patents are hereby incorporated by reference in their entireties.

Papermaking sludge typically contains a rather high amount of $CaCO_3$ (up to 20%–50% of solids or more). In the presence of many acids, $CaCO_3$ is solubilized as a result of conversion into the acid-anion salt in the reaction mixture. Since papermaking sludge often contains an organic fraction (cellulose, lignin, hemicellulose), some organic materials, pentose sugars in particular, can be extracted by acids as well, thereby decreasing the purity of the target calcium salt. Also, $CaCO_3$ in the sludge is typically accompanied by aluminosilicates (clay) and other minerals (as pigments, fillers, etc.), such as those based on magnesium, potassium and others. These can be partially extracted with acids as well. Obviously, the extent of acid extraction/solubilization of the inorganic and organic components, making the target calcium salt less pure, greatly depends on conditions of the sludge treatment with acids, nature of the acid, the acid concentration, and contact time with the acid in particular.

Combustion (calcination, or incineration) of sludge eliminates the organic components of the material and makes the material more compact. However, this process may also change the chemistry of the inorganic constituents. Calcination of $CaCO_3$ in the presence of aluminosilicates, for example, leads to formation of calcium aluminosilicates and other complex minerals (see above). Their chemical properties differ significantly from those of calcium carbonate, as illustrated by the following comparative examples.

Comparative Example 1. Five types of materials were tested for their alkalinity, that is their ability to increase pH of water in standard conditions (10 mg/10 mL at room temperature):

(1) CaO (commercial preparation), (2) $CaCO_3$ (commercial preparation), (3) $CaCO_3$, calcined at 825° C., 900° C., and 1000° C. (weight loss 44.0±0.4% compare with the initial $CaCO_3$), (4) Dry paper sludge ($CaCO_3$ content 23%, total ash content 32.7%), and (5) Paper sludge as in (4), but calcined at 825° C., 900° C., and 1000° C. (weight loss 24.0±0.4%); calcium content 30.0±0.4%, which translates into 42.0±0.6% CaO equivalent.

Dry paper sludge (4) and pure $CaCO_3$ (2) showed similar alkalinity: the pH increased to 9.2–9.6, though it took more time and/or a higher amount for the sludge to reach the same pH value as $CaCO_3$.

Calcined $CaCO_3$ (all three samples, calcined at the temperatures indicated above) showed the same alkalinity as pure CaO: all produced a rapid "pH-jump" to 12.6–12.7. Even 20% of the amount taken, i.e., 2 mg of CaO, produced a rapid pH increase to 12.0.

Calcined sludge (all three samples, calcined at the temperatures indicated above) produced rather slow increase in pH, and only to 10.9–11.2.

This Example shows that the calcined paper sludge does not contain CaO. Besides, calcium compound(s), formed as a result of calcination of the sludge, are obviously less reactive than calcium oxide.

Comparative Example 2. Three types of materials were tested for their exothermic reactivity upon contact with water, i.e., their ability to increase temperature of water in standard conditions (0.5 g/0.5 mL, starting at room temperature):

(1) CaO (commercial preparation), (2) $CaCO_3$, calcined at 1000° C., (3) Calcined paper sludge as in Comparative Example 1 (calcined at 825° C. and 1000° C., calcium content 30.0±0.4%, translating into 42.0±0.6% of CaO equivalent).

Freshly calcined $CaCO_3$ showed the highest exothermic effect, temperature 86.5° C. was reached in 40 seconds.

Commercial CaO showed increase in temperature up to a maximum at 59° C. reached in 10.5 min.

Calcined sludge did not show any noticeable increase in temperature (i.e., less than 0.5.

This Example shows again that the calcined paper sludge does not contain CaO. Besides, calcium compound(s), formed as a result of calcination of the sludge, obviously are quite different chemical(s) from calcium oxide.

In a first aspect, the invention comprises extraction of minerals from a papermaking sludge. The sludge generally contains a mix of common components of plant materials with minerals ($CaCO_3$ and clay, in particular, that typically can account for a significant fraction of the composition of paper sludge), and is mixed with a solution of an inorganic or organic acid—generally 0.1% to 35% by weight, preferably 2% to 20%, and most preferably 3% to 8% by weight; the optimal concentration depends on process conditions (in particular, calcium carbonate content in the processed papermaking sludge) and the desirable concentration of the target salt in the solution produced. In preferred embodiments, the mixture is combined with 3% to 6% HCl; 2% to 25%, and most preferably 8%, $HNO_3$; 2% to 30%, and most preferably 8%, acetic acid. Generally, the amount of acid added into the reaction mixture preferably is 0.8 to 2.0 times the stoichiometric calcium carbonate content in the mixture, more preferably 0.8 to 1.2 times the stoichiometric content, and most preferably matched to the stoichiometric content of calcium carbonate in the mixture. The acid-containing mixture is incubated (with agitation, if desired, to shorten the reaction time) to solubilize the desired minerals, following which the liquid phase is isolated, and mineral salts recovered therefrom.

In a second aspect, the invention comprises extraction of minerals from ash produced by incineration of a papermaking sludge. The ash is combined with water and mixed with a solution of an inorganic or organic acid—generally 2% to 35% by weight, preferably 5% to 25%, and most preferably 8% to 14% by weight; the optimal concentration depends on process conditions (in particular, calcium carbonate content in the ash) and the desirable concentration of the target salt in the solution produced. In preferred embodiments, the mixture is combined with 8% to 14% HCl; 5% to 20%, and most preferably 8% to 10%, $HNO_3$; 5% to 20%, and most preferably 10% to 13%, acetic acid. Generally, the amount of acid added into the reaction mixture preferably is 0.8 to 2.0 times the stoichiometric calcium carbonate content in the mixture, more preferably 0.8 to 1.2 times the stoichiometric content, and most preferably matched to the stoichiometric content of calcium carbonate in the mixture. Once again, the acid-containing mixture is incubated (with agitation, if desired, to shorten the reaction time) to solubilize the desired minerals, following which the liquid phase is isolated, and mineral salts recovered therefrom.

After completion of calcium solubilization, which can be verified by determination of the calcium concentration or content in the bulk solution, the liquid is separated from the solids by conventional means, such as filtration, centrifugation, or dewatering using belt presses, screw presses, filters and the like, or other suitable separation method. The solid residue comprising cellulose fiber, lignin, and minerals, such as clay, kaolin, other aluminosilicates, etc., can be utilized in other applications, serving as cat litter or an oil absorbant.

The calcium salt obtained in the liquid is used in the form of that liquid or in a concentrated form (e.g., by evaporation of the water phase), or recovered by precipitation as a water-insoluble calcium compound, e.g., calcium carbonate. The precipitation is performed using water-soluble carbonates or bicarbonates, or by carbonation of the water solution with carbon dioxide, or by any other suitable carbonation method. Using different carbonation methods (e.g., at different temperatures), different concentrations of water-soluble calcium salts, different flow rate of carbon dioxide, etc., different morphological forms of calcium carbonate are produced as precipitates for use in the many known applications of calcium carbonate.

Using the approach of the present invention, it is possible to obtain solutions of calcium chloride, calcium nitrate, and calcium acetate from a number of papermaking sludge materials, and a number of their incineration ash preparations obtained at various thermal conditions.

DETAILED DESCRIPTION OF THE PREFERRED EMBODIMENTS

EXPERIMENTAL PROCEDURES

1. Determination of calcium: the procedure based on titration with EDTA

TAPPI procedure T 247 cm-83 (Classical Method-1983) was used for calcium determination in sludge and pulp. The procedure is based on EDTA titration of $HNO_3$- soluble calcium in ashed sludge and pulp. EDTA forms a highly-colored water-soluble complex with calcium, while other metal ions present are masked with triethanolamine. The ash was placed in 10 mL of Milli-Q and 3 mL of 5 M nitric acid (325 mL of concentrated nitric acid diluted to 1 L with water) was added. The mixture was heated for 5–10 min on a steam bath, transferred into a 300-mL flask, the volume was adjusted to 100 mL, 5 mL of 8 M KOH solution was added, the flask was shaken occasionally for 5 min, and 5 mL of triethanolamine (diluted 10 times), and then 2 mL of hydroxylamine hydrochloride solution (2 g/100 mL) were added, along with 100 mg of cal-red indicator. The mixture was titrated with 0.02 M EDTA solution to a color change from red-wine to blue. Calcium content (in %) was calculated as EDTA(mL)×0.08016/g of dry weight ash.

2. Determination of solids and calcium content in acid calcium extracts, dried at 105° C. and combusted at 525° C.

Weight determination of compounds dissolved in acid water extracts, described below as "solids," was performed by evaporation of a 10-mL sample at 105° C.—until a constant weight was attained—using the Mettler Infrared Moisture Analyzer, or a programmable oven.

Salts of calcium and other metals, typically present in acid extracts of papermaking sludge, often contain bound water. Since this water often remains with salts dried at 105° C., calcium (as well as other metals) are typically "diluted" when determined in the dried extracts.

Examples of such calcium salts include: $CaCl_2.H_2O$, $CaCl_2.2H_2O$ (loses both water molecules at 200° C.), calcium chloride aluminate $3CaO.Al_2O_3.CaCl_2.10H_2O$ (loses 1 water molecule at 105° C. and 8 water molecules at 350° C.), $Ca(NO_3)_2.3H_2O$, $Ca(NO_3)_2.4H_2O$ water at 132° C.), $Ca(CH_3COO)_2.2H_2O$ (loses 1 water molecule at 84° C.), $Ca(CH_3COO)_{2.H2}O$ (loses the water molecule at about 150° C., converts into $CaCO_3$ at 160° C.), $CaCO_3.6H_2O$. If not taken into consideration, these bound water molecules affect analytical results. Some other bound water-containing compounds that might easily get into the sludge acid-extracted solids and their carbonated precipitates, and therefore affect analytical data, are $Mg(CH_3COO)_2.4H_2O$, $Mg(CO_3).3H_2O$, $Mg(CO_3).5H_2O$, and others.

To eliminate the bound water as much as possible without substantially altering the principal chemical composition of the solids, the solids were dried at 105° C., analyzed, and then combusted at 525° C. Reduction in weight as a result of the combustion was typically ascribed either to a combination of organic materials and bound water (when a whole sludge extracts were analyzed), or to bound water alone (when extracts of the ashed sludge were analyzed). Calcium acetate on heating above 160° C. decomposes to $CaCO_3$ and acetone. Therefore, calcium content in the combusted solids, extracted with acetic acid, can be indicative of the purity of the originally solubilized calcium acetate. For example, if elemental calcium content in the combusted solids is 40% by weight (corresponding to pure $CaCO_3$), the acetic acid calcium extract contains practically pure calcium acetate.

Calcium in the acid extracts dried at 105° C. and 525° C. was determined using TAPPI procedure T 247 cm-83, as described above. Calcium in liquid acid extracts was determined in 1-mL or 3-mL aliquots also processed according to said TAPPI procedure.

EXAMPLE 1

This example describes solubilization of calcium (in the form of calcium chloride) from mixed office sludge by diluted hydrochloric acid, in a proportion of 1.56 times the stoichiometric amount of calcium carbonate content in the sludge. The initial sludge material had a moisture content of 43.4%, an ash content of 32.7% (dry matter), and an elemental calcium content of 9.2%, representing a calcium carbonate content of 23% in the whole dried sludge. Moisture content was determined either by heating the material in a temperature-programmed furnace at 105° C. to constant weight, typically overnight, or using a Mettler Moisture Analyzer. Ash content was determined by combustion of the material overnight in a furnace at 525° C.

The solubilization was performed as follows. 33.4 mL (39.75 g) of 37.4% hydrochloric acid was added to 116.6 mL of water, and the resulting 150 mL of 8.3% (v/v) or 9.9% (w/w) HCl was added to 100 g of the wet sludge (taking into account water content in the sludge, the final concentration of HCl in the liquid was 6.5% v/v, or 7.7% w/w). That amount of hydrochloric acid was 56% higher compared with the stoichiometric amount needed for complete solubilization of the calcium carbonate present in the sludge. The mixture was placed in an incubator-shaker, and incubated for 4 hrs at 500 rpm, room temperature. Supernatant was then decanted, the solid residue pressed, and 118 mL of liquid was collected. The liquid contained 10.6% of solids, as was shown by evaporation of a 5-mL sample at 105° C.

Elemental calcium content in the dried solids was 25.7%, translating into 71.3% of $CaCl_2$, or 94.4% of $CaCl_2.2H_2O$ of the total solids.

Elemental calcium content in the liquid extract was 27,570 ppm, or 2.76%. This translates into 7.65% of $CaCl_2$ or 10.13% of $CaCl_2.2H_2O$ in the extract, that is, 72.2% and 95.6% of total solids, respectively.

Combustion of the dried solids at 525° C. reduced their weight by 19.2% (the theoretical value for transition of $CaCl_2.2H_2O$ into $CaCl_2$ is 24.5%), and the calcium content in the combusted solids was determined to be 28.7%, translating into 80% of $CaCl_2$ in the total solids.

41.3 g of the washed and dried sludge residue was collected. The calcium content in the solid residue was 0.8%. The material contained primarily cellulose, lignin, and clay.

The following Table 1 shows analysis of the liquid obtained as in Example 1.

TABLE 1

Analysis of calcium chloride solution, obtained by solubilization of calcium from mixed office paper sludge with hydrochloric acid (1.56 times the stoichiometric calcium carbonate content in the sludge)

| Analysis | ppm (mg/L) | % of Ca content |
|---|---|---|
| Calcium | 25,300 | 100.00 |
| Aluminum | 514 | 2.03 |
| Magnesium | 430 | 1.70 |
| Silicon | 130 | 0.51 |
| Iron | 68 | 0.27 |
| Potassium | 17 | 0.07 |
| Heavy Metals as Lead | <30 | <0.12 |
| Titanium | 0.88 | 0.003 |
| Organic Carbon | 1,032 | 4.08 |
| Chloride | 68,000 | |
| Calcium Chloride | 106,000 | |

EXAMPLES 2 AND 3

The procedure of Example 1 was repeated, but with the difference that the amount of hydrochloric acid added to the sludge was the 1.2 times the stoichiometric calcium carbonate content in the sludge. Two separate experiments were performed, one with 100 g of the wet sludge, another with 250 g of the wet sludge.

(EXAMPLE 2) 24.9 mL (29.63 g) of 37.4% HCl was added to 125.1 mL of water, and the resulting 150 mL of 6.2% (v/v) or 7.2% (w/w) HCl was added to 100 g of the wet sludge (taking into account water content in the sludge, the final concentration of HCl in the liquid was 4.8% v/v, or 5.6% w/w). Incubation of the reaction mixture in the incubator-shaker took place for 30 min at 500 rpm. 121 mL of liquid was collected. The liquid contained 7.7% of solids (dried at 105° C.). Elemental calcium content in the dried solids was 30.0%, translating into 83% CaCl, or 110% $CaCl_2.2H_2O$ relative to the total solids.

Combustion of the dried solids at 525° C. reduced their weight by 13.9% (the theoretical value for transition of $CaCl_2.2H_2O$ into $CaCl_2$ is 24.5%), and the calcium content in the combusted solids was determined to be 33.6%, translating into 93% of $CaCl_2$ in the total solids.

(EXAMPLE 3) 63.0 mL (75.0 g) of 37.4% HCl was added to 437 mL of water, and the resulting 500 mL of 4.7% (v/v) or 5.5% (w/w) HCl was added to 250 g of the wet sludge (taking into account water content in the sludge, the final concentration of HCl in the liquid was 3.9% v/v, or 4.5% w/w). The mixture was agitated with a propeller mixer for 30 min. 440 mL of liquid was collected. The liquid contained 8.2% solids (dried at 105° C.). Elemental calcium content in the dried solids was 26.2%, translating into 73% CaCl, or 96% $CaCl_2.2H_2O$ relative to the total solids.

Combustion of the dried solids at 525° C. reduced their weight by 17.5% (the theoretical value for transition of $CaCl_2.2H_2O$ into $CaCl_2$ is 24.5%), and the calcium content in the combusted solids was determined to be 33.6%, translating into 93% $CaCl_2$ in the total solids.

102.7 g of the unwashed and dried sludge residue was collected, with an average calcium content 4.9%. Washing of the residue with 5-fold excess of water resulted in 98%-recovery of the solid residue and 99%-recovery of wash waters, with solids content 0.58%. Drying at 105° C. (wash-water temperature) resulted in solids having a calcium content 30.3%, translating into 84% $CaCl_2$, or 111% $CaCl_2.2H_2O$.

EXAMPLES 4 AND 5

The procedure of Example 1 was repeated, but with the difference that the amount of hydrochloric acid added to the sludge was stoichiometric with respect to the calcium carbonate content in the sludge.

(EXAMPLE 4) 21.4 mL (25.45 g) of 37.4% HCl was added to 128.6 mL of water, and the resulting 150 mL of 5.3% (v/v) or 6.3% (w/w) HCl was added to 100 g of the wet sludge (taking into account water content in the sludge, the final concentration of HCl in the liquid was 4.1% v/v, or 4.9% w/w). The reaction mixture was placed into an incubator-shaker for 30 min at 300 rpm. 115 mL of liquid was collected. The liquid contained 6.9±0.2% of solids (representing the average of two separate drying procedures at 105° C.). Elemental calcium content in the dried solids was determined to be 29.8%, translating into 83% $CaCl_2$, or 110% $CaCl_2.2H_2O$.

Combustion of the dried solids at 525° C. reduced their weight by 18.6% (the theoretical value for transition of $CaCl_2.2H_2O$ into $CaCl_2$ is 24.5%), and the calcium content in the combusted solids was determined to be 31.8%, translating into 88% of $CaCl_2$ in the total solids. 43.2 g of the washed and dried sludge residue was collected. The calcium content in the solid residue was determined to be 2.6%.

(EXAMPLE 5) 51.9 mL (61.8 g) of 37.4% HCl was added to 448.1 mL, of water, and the resulting 500 mL of 3.9% (v/v) or 4.5% (w/w) HCl was added to 250 g of the wet sludge (taking into account water content in the sludge, the final concentration of HCl in the liquid was 3.2% v/v, or 3.7% w/w). The mixture was agitated with a propeller mixer for 30 min. 400 mL of liquid was collected. The liquid contained 5.9% solids (dried at 105° C.). Elemental calcium content in the dried solids was determined to be 28.7%, translating into 80% CaCl, or 105% $CaCl_2.2H_2O$ relative to the total solids.

Combustion of the dried solids at 525° C. reduced their weight by 14.4% (the theoretical value for transition of $CaCl_2.2H_2O$ into $CaCl_2$ is 24.5%), and the calcium content of the combusted solids was determined to be 32.9%, translating into 91% of $CaCl_2$ in the total solids.

97.3 g of the unwashed and dried sludge residue was collected, with an average calcium content of 6.6%. Washing of the residue with a 5-fold excess of water resulted in 98% recovery of both the solid residue and the wash waters. Elemental calcium content of the solid residue, dried at 105° C., was determined to be 4.7%. Drying of the wash waters at 105° C. resulted in solids (0.53% by weight) with calcium content of 30.1%, translating into 84% $CaCl_2$, or 111% $CaCl_2.2H_2O$.

The following Table 2 shows analysis of the liquid obtained as in Example 4.

TABLE 2

Analysis of calcium chloride solution, obtained by solubilization of calcium from mixed office paper sludge with HCl (the stoichiometric amount of the acid relative to calcium carbonate content in the sludge was used)

| Analysis | ppm (mg/L) | % of Ca content |
|---|---|---|
| Calcium | 32,820 | 100.00 |
| Aluminum | 276 | 0.84 |
| Magnesium | 338 | 1.03 |
| Silicon | 99 | 0.30 |
| Iron | 34 | 0.10 |
| Potassium | 21 | 0.06 |
| Heavy Metals as Lead | <30 | <0.09 |
| Titanium | 0.17 | 0.0005 |
| Organic Carbon | 765 | 2.33 |
| Chloride | 44,200 | |
| Calcium Chloride | 69,200 | |

EXAMPLES 6 AND 7

The procedure of Example 1 was repeated, but with the difference that the amount of HCl added to the sludge was the 0.8 times the stoichiometric calcium carbonate content in the sludge.

(EXAMPLE 6) 16.6 mL (19.75 g) of 37.4% HCl was added to 133.4 mL of water, and the resulting 150 mL of 4.1% (v/v) or 4.9% (w/w) HCl was added to 100 g of the wet sludge (taking into account the water content of the sludge, the final concentration of HCl in the liquid was 3.2% v/v, or 3.8% w/w). The reaction mixture was placed into an incubator-shaker for 30 min at 500 rpm. 125 mL of liquid was collected. The liquid contained 5.9% solids (dried at 105° C.). Elemental calcium content in the dried solids was 31.6%, translating into 88% CaCl, or 116% $CaCl_2.2H_2O$ relative to the total solids.

Combustion of the dried solids at 525° C. reduced their weight by 18.6% (the theoretical value for transition of $CaCl_2.2H_2O$ into $CaCl_2$ is 24.5%), and calcium content in the combusted solids was determined to be 32.8%, translating into 91% of $CaCl_2$ in the total solids.

48.53 g of the unwashed and dried sludge residue was collected, with an average calcium content 5.7%; washing with 250 mL of water resulted in 48.03 g of washed dry material with a calcium content of 3.0%. 245 mL of wash waters were recovered, with a solids content of 0.68% and a calcium content in the solids of 29.2%.

(EXAMPLE 7) 42.0 mL (50.0 g) of 37.4% HCl was added to 458 mL of water, and the resulting 500 mL of 3.1% (v/v) or 3.7% (w/w) HCl was added to 250 g of the wet sludge (taking into account water content in the sludge, the final concentration of HCl in the liquid was 2.6% v/v, or 3.0% w/w). The mixture was agitated with a propeller mixer for 30 min. 400 mL of liquid was collected. The liquid contained 5.8% of solids (dried at 105° C.). Elemental calcium content in the dried solids was determined to be 29.8%, translating into 83% CaCl, or 110% $CaCl_2.2H_2O$ relative to the total solids.

Combustion of the dried solids at 525° C. reduced their weight by 17.5% (the theoretical value for transition of $CaCl_2.2H_2O$ into $CaCl_2$ is 24.5%), and the calcium content in the combusted solids was determined to be 33.0%, translating into 92% $CaCl_2$ relative to the total solids.

111.8 g of the unwashed and dried sludge residue was collected, with an average calcium content 7.0%. Washing of the residue with a 5-fold excess of water resulted in 98% recovery of the solid residue and 96% recovery of the wash waters. Elemental calcium content of the washed solid residue, dried at 105° C., was determined to be 4.2%. Drying of the wash waters at 105° C. resulted in solids (0.49% by weight) with a calcium content of 29.1%, translating into 81% $CaCl_2$, or 107% $CaCl_2.2H_2O$.

EXAMPLES 8 THROUGH 10

The procedure of Example 7 was repeated, but with the difference that the reaction time was 5 min and 15 min. The example with the reaction time 30 min was also repeated. The data obtained are listed in the following Table 3.

TABLE 3

Solubilization of calcium from mixed office paper sludge with HCl (in an amount equal to 0.8 times the stoichiometric amount of calcium carbonate in the sludge)

| EXAM-PLE | Time, min | Solids after extraction, % | $CaCl_2$ in dried solids, % | Weight loss at combustion, % | $CaCl_2$ in the combusted solids, % |
|---|---|---|---|---|---|
| 8 | 5 | 5.0 | 60 | 23 | 89 |
| 9 | 15 | 5.3 | 65 | 27 | 91 |
| 10 | 30 | 4.7 | 86 | 24 | 93 |

It is apparent that an increase in reaction time from 5 min to 15 min. and further to 30 min, results in a higher purity of the target calcium chloride. This is probably due to the slower solubilization of calcium compared with other components of the sludge that are also solubilized by HCl.

EXAMPLES 11 AND 12

The procedure of Example 3 was repeated, but with the difference that the reaction time was 5 min and then 15 min. The data obtained are listed in the following Table 4 together with those of Example 3.

TABLE 4

Solubilization of calcium from mixed office paper sludge with HCl (in an amount equal to 1.2 times the stoichiometric amount of calcium carbonate in the sludge)

| EXAM-PLE | Time, min | Solids after extraction, % | $CaCl_2$ in dried solids, % | Weight loss at combustion, % | $CaCl_2$ in the combusted solids, % |
|---|---|---|---|---|---|
| 11 | 5 | 8.9 | 64 | 21 | 63 |
| 12 | 15 | 8.4 | 57 | 16 | 83 |
| 3 | 30 | 8.2 | 73 | 18 | 93 |

As was also shown in Examples 7 through 10, it is apparent that an increase in reaction time from 5 min to 15 min, and further to 30 min, results in a higher purity of the target calcium chloride. It is also apparent from the data in Tables 3 and 4 that a higher purity of the material combusted at 525° C. (last column in both tables) results from a loss of 16% to 27% of volatile solids (bound water and other combustible compounds).

EXAMPLES 13 THROUGH 23

The procedure of Examples 3, 5, and 7 were repeated (for stoichiometric ratios of HCl to $CaCO_3$ in the sludge equal to 1.2, 1.0, and 0.8), but with the difference that the reaction time was 60 min and then 120 min. The data obtained are listed in the following tables 5–8 together with the data of Examples 3, 5, and 7–12.

(EXAMPLE 13) The stoichiometric ratio was 0.8 and the reaction time was 30 min.
(EXAMPLE 14) The stoichiometric ratio was 0.8 and the reaction time was 60 min.
(EXAMPLE 15) The stoichiometric ratio was 0.8 and the reaction time was 120 min.
(EXAMPLE 16) The stoichiometric ratio was 1.0 and the reaction time was 5 min.
(EXAMPLE 17) The stoichiometric ratio was 1.0 and the reaction time was 15 min.
(EXAMPLE 18) The stoichiometric ratio was 1.0 and the reaction time was 30 min.
(EXAMPLE 19) The stoichiometric ratio was 1.0 and the reaction time was 60 min.
(EXAMPLE 20) The stoichiometric ratio was 1.0 and the reaction time was 120 min.
(EXAMPLE 21) The stoichiometric ratio was 1.0 and the reaction time was 30 min.
(EXAMPLE 22) The stoichiometric ratio was 1.2 and the reaction time was 60 min.
(EXAMPLE 23) The stoichiometric ratio was 1.2 and the reaction time was 120 min.

TABLE 5

Solubilization of calcium from mixed office paper sludge with HCl.
The concentration of extractable solids is shown for different
stoichiometric proportions of the acid relative to calcium carbonate
content in the sludge, and for different reaction times

| Time, min | Stoichiometric ratio of HCl to CaCO$_3$ in the sludge | | | Average concentration, % |
|---|---|---|---|---|
| | 0.8 | 1.0 | 1.2 | |
| 5 | 5.0 | 6.3 | 8.9 | 6.7 ± 2.0 |
| 15 | 5.3 | 6.4 | 8.4 | 6.7 ± 1.6 |
| 30 | 5.1 ± 0.6 | 5.8 ± 0.2 | 7.6 ± 0.5 | 6.2 ± 1.3 |
| 60 | 4.6 | 5.9 | 7.3 | 5.9 ± 1.4 |
| 120 | 4.9 | 5.7 | 7.1 | 5.9 ± 1.1 |
| Average concentration, % | 5.0 ± 0.3 | 6.0 ± 0.3 | 7.8 ± 0.8 | |

TABLE 6

Solubilization of calcium from mixed office paper sludge with HCl.
The fraction of CaCl$_2$ (anhydrous) in the extracted solids,
dried at 105° C., is shown for different stoichiometric
proportions of the acid relative to calcium carbonate in the sludge,
and for different reaction times

| Time, min | Stoichiometric ratio of HCl to CaCO$_3$ in the sludge | | | Average CaCl$_2$ fraction, % |
|---|---|---|---|---|
| | 0.8 | 1.0 | 1.2 | |
| 5 | 60 | 77 | 64 | 67 ± 9 |
| 15 | 65 | 76 | 57 | 66 ± 10 |
| 30 | 84 ± 2 | 82 ± 2 | 77 ± 4 | 81 ± 5 |
| 60 | 88 | 87 | 84 | 86 ± 2 |
| 120 | 80 | 81 | 84 | 82 ± 2 |
| Average CaCl$_2$ fraction, % | 77 ± 12 | 81 ± 4 | 74 ± 11 | 77 ± 10 |

TABLE 7

Solubilization of calcium from mixed office paper sludge with HCl.
Weight loss reflects drying of solids at 105° C., folloiwng combustion
at 525° C. The data are shown for the different stoichiometric
proportions of the acid relative to calcium carbonate in the sludge, and
for different reaction times

| Time, min | Stoichiometric ratio of HCl to CaCO$_3$ in the sludge | | | Average weight loss, % |
|---|---|---|---|---|
| | 0.8 | 1.0 | 1.2 | |
| 5 | 23 | n.d. | 21 | 22 ± 2 |
| 15 | 27 | n.d. | 16 | 22 ± 7 |
| 30 | 17 ± 6 | 13 ± 2 | 15 ± 3 | 15 ± 5 |
| 60 | 8 | 9 | 13 | 10 ± 3 |
| 120 | 11 | 19 | 17 | 16 ± 4 |
| Average weight loss, % | 17 ± 8 | 13 ± 4 | 16 ± 3 | 16 ± 7 |

TABLE 8

Solubilization of calcium from mixed office paper sludge with HCl.
The fraction of CaCl$_2$ (anhydrous) in the solids, combusted at
525° C., is shown for different stoichiometric proportions of
the acid, and for different reaction times

| Time, min | Stoichiometric ratio of HCl to CaCO$_3$ in the sludge | | | Average CaCl$_2$ fraction, % |
|---|---|---|---|---|
| | 0.8 | 1.0 | 1.2 | |
| 5 | 89.1 | n.d. | 62.7 | 76 ± 19 |
| 15 | 91.0 | n.d. | 83.3 | 87 ± 5 |
| 30 | 91.4 ± 0.2 | 90.0 ± 1.3 | 88.8 ± 4.4 | 90 ± 3 |
| 60 | 91.3 | 93.5 | 84.9 | 90 ± 4 |
| 120 | 92.1 | 89.4 | 87.4 | 90 ± 2 |

It apparent from Tables 5–8 that:

The concentration of the extracted solids generally increased with increasing HCl concentration in the reaction mixture, The fraction of CaCl$_2$ in the extracted solids (dried at 105° C.), calculated as the anhydrous salt, does not depend noticeably on the amount of HCl in the reaction mixture (at least in the range tested) and on the reaction time, and is equal to 77±10%, When combusted at 525° C., the extracted solids lose 16±7% of their weight, apparently in the form of bound water (since they contain only a small amount of organic materials, as Tables 1 and 2 show), The fraction of CaCl$_2$ in the combusted solids increases with decreasing amounts of HCl in the reaction system, reaching 91%–92% at a stoichiometric proportion of HCl to CaCO$_3$ in the reaction system equal to 0.8, and During the initial period of the reaction (the first 5 to 15 min in the conditions described) the fraction of CaCl$_2$ was rather low, and reached 91%–92% at 30–60–120 min.

In EXAMPLE 15, after 120 min of reaction with a stoichiometric amount of HCl equal to 0.8, 405 mL of the extract was recovered along with 93.5 g of dry unwashed solid residue, with elemental calcium content 6.2%. After the residue was washed and dried, it contained 5.4% calcium. The solids recovered from the wash waters and dried at 105° C. contained 27.4% elemental calcium, translating into 76% CaCl$_2$ content. Combustion of these solids at 525° C. increased the calcium content to 31.6%, that is, 87.7% CaCl$_2$.

In EXAMPLE 20, after 120 min of reaction with the stoichiometrically equivalent amount of HCl, 425 mL of the extract was recovered along with 104 g of dry unwashed solid residue, with an elemental calcium content of 7.8%. After the residue was washed and dried, it contained 2.1% calcium. The solids recovered from the wash waters and dried at 105° C. contained 29.1% elemental calcium, translating into 81% CaCl$_2$ content. Combustion of these solids at 525° C. increased the calcium content to 33.1%, that is, 91.9% CaCl$_2$.

In EXAMPLE 23, after 120 min of reaction with a stoichiometric proportion of HCl equal to 1.2, 385 mL of the extract was recovered along with 112 g of dry unwashed solid residue, with an elemental calcium content of 5.0%. After the residue was washed and dried, it contained 1.9% calcium. The solids recovered from the wash waters and dried at 105° C. contained 27.2% elemental calcium, translating into 75.5% CaCl$_2$ content. Combustion of these solids at 525° C. increased the calcium content to 33.7%, that is 93.5% CaCl$_2$.

EXAMPLE 24

The procedure of Example 1 was repeated, but with the difference that the amount of HCl added to the sludge was 2.05 times stoichiometric amount of calcium carbonate in the sludge, and the total amount of the diluted HCl added (as well as the conditions of the reaction) differed from Example 1. 82 mL of 20% (v/v) HCl (23.8% w/w) was added to 100 g of the wet sludge (taking into account water content in the sludge, the HCl concentration in the reaction system was 13.1% v/v), agitated, and incubated overnight at room temperature. Then 82 mL of water were added, making the final HCl concentration 7.9% (v/v) or 9.1% (w/w). 96 mL of the resulting liquid was collected, and this determined to contain 15.0±0.3% solids (based on an average of two separate drying procedures at 105° C.). Elemental calcium content in the dried solids was 12.6%, translating into 35% CaCl or 46% $CaCl_2.2H_2O$ relative to total solids.

Combustion of the dried solids at 525° C. reduced their weight by 41% (the theoretical value for transition of $CaCl_2.2H_2O$ into $CaCl_2$ is 24.5%), and the calcium content in the combusted solids was 24.4%, translating into 68% $CaCl_2$.

38.3 g of the washed and dried sludge residue was collected. The calcium content in the residue was 1.2%.

EXAMPLE 25

The procedure of Example 24 was repeated, but with a different order of mixing the reagents and separating the resulting liquid from the residual solids. 82 mL of 20% (v/v) HCl was first diluted with 82 mL of water, and then the resulting 10% (v/v) HCl was added to 100 g of the wet sludge. The final concentration of the reagents in the reaction mixture was the same as in Example 23. After overnight incubation the supernatant was decanted, and the collected insoluble sludge residue placed into a Buchner funnel and subjected to vacuum filtration using house vacuum. 132 mL total of the liquid was collected and filtered through Whatman No. 1 filter paper. Solids content in the collected liquid was 12.0%, as shown by evaporation of a 10-mL sample at 105° C. Combustion of the dried solids at 525° C. reduced their weight by 43.5% (the theoretical value for transition of $CaCl_2.2H_2O$ into $CaCl_2$ is 24.5%). 35.8 g of the washed and dried sludge residue was collected.

EXAMPLES 26 THROUGH 29

The procedures of Examples 8 through 10 and 14 were repeated, but with the difference that the initial material was fines and minerals separated from mixed office sludge, and the amount of the material was 317 g. This material had a moisture content 56.9%, an elemental calcium content of 12.04% (dry matter), giving a calcium carbonate content of 30.1% in the whole dried sludge. 52 mL (61.9 g) of 37.4% HCl was added to 448 mL of water, and the resulting 500 mL of 3.9% (v/v) or 4.5% (w/w) HCl was added to 317 g of the wet sludge (taking into account water content in the sludge, the final concentration of HCl in the liquid was 2.9% v/v, or 3.4% w/w). That stoichiometric proportion of HCl was 0.8 relative to a complete solubilization of the calcium carbonate present in the initial material (41.1 g of calcium carbonate require 80.2 g, or 67.4 mL, of 37.4% HCl). The mixture was agitated with a propeller mixer. The data obtained are listed in Table 9.

TABLE 9

Solubilization of calcium from fines and minerals (obtained from mixed office paper sludge) with HCl (stoichiometric proportion of 0.8 relative to calcium carbonate content in the sludge)

| EXAMPLE | Time, min | Solids after extraction, % | $CaCl_2$ in dried solids, % | Weight loss at combustion, % | $CaCl_2$ in the combusted solids, % |
|---|---|---|---|---|---|
| 26 | 5 | 5.9 | 72 | 24 | 96 |
| 27 | 15 | 5.9 | 72 | 28 | 93 |
| 28 | 30 | 6.1 | 76 | 31 | 92 |
| 29 | 60 | 6.6 | 76 | 25 | 92 |
| Average | | 6.1 ± 0.3 | 74 ± 2 | 27 ± 3 | 93 ± 2 |

As in Examples 7 through 12, it is apparent that an increase in reaction time (up to 30–60 min) generally results in a higher purity of the target calcium chloride, probably because of the slower solubilization of calcium compared with other components of the sludge that are also solubilized by HCl.

EXAMPLES 30 THROUGH 33

The procedures of Examples 26 through 29 were repeated, but with the difference that the amount of HCl was stoichiometrically equivalent to calcium carbonate in the material (fines and minerals separated from mixed office sludge), and the amount of the material was 300 g. 63.5 mL (75.6 g) of 37.4% HCl was added to 436.5 mL of water, and the resulting 500 mL of 4.7% (v/v) or 5.5% (w/w) HCl was added to 300 g of the wet sludge (taking into account water content in the sludge, the final concentration of HCl in the liquid was 3.5% v/v, or 4.1% w/w). That amount of HCl was the stoichiometric equivalent needed for complete solubilization of the calcium carbonate present in the initial material. The mixture was agitated with a propeller mixer. The data obtained are listed in the following Table 10.

TABLE 10

Solubilization of calcium from fines and minerals (obtained from mixed office paper sludge) with HCl stoichiometrically equivalent to calcium carbonate content in the sludge)

| EXAMPLE | Time, min | Solids after extraction, % | $CaCl_2$ in dried solids, % | Weight loss at combustion, % | $CaCl_2$ in the combusted solids, % |
|---|---|---|---|---|---|
| 30 | 5 | 6.5 | 70 | 33 | 91 |
| 31 | 15 | 6.9 | 76 | 23 | 93 |
| 32 | 30 | 6.6 | 85 | 23 | 94 |
| 33 | 60 | 7.1 | 85 | 21 | 96 |
| Average | | 6.8 ± 0.3 | 74 ± 2 | 25 ± 5 | 93 ± 2 |

As in Examples 7 through 12, and 26 through 29, it is apparent that an increase in reaction time (up to 30–60 min) generally results in a higher purity of the target calcium chloride.

EXAMPLE 34

The procedure of Example 1 was repeated, but with the difference that diluted nitric acid was used for solubilization of calcium (in the form of calcium nitrate) from mixed office sludge from the same source as in Example 1, and of a similar composition. The initial sludge material had a moisture content of 38.4%, an ash content 31.5% (dry matter), and an elemental calcium content 8.16%, translating into a calcium carbonate content of 20.4% in the whole dry sludge. 150 mL of 20% nitric acid (143 mL of 69.9% nitric acid diluted to 500 mL with water) was added to 100 g of the wet sludge. Taking into account water content in the sludge, the nitric acid concentration in the reaction system was 15.9% v/v, i.e., 1.9 times the stoichiometric content of calcium carbonate content in the sludge. 90 mL of liquid was collected. The liquid contained 10.4±0.2% of solids (based on an average of two separate experiments), as was shown by evaporation of a 10-mL sample at 105° C. The theoretical concentration of calcium nitrate formed would be 10.9%. Elemental calcium content in the dried solids was 18.3±0.5 (based on three separate measurements), translating into 75±2% $Ca(NO_3)_2$, or 108±3% $Ca(NO_3)_2.4H_2O$.

41.6 g of the washed and dried sludge residue was collected.

EXAMPLE 35

The procedure of Example 34 was repeated, but with the difference that 200 mL of 20% nitric acid was used for solubilization of calcium, representing 2.53 times the stoichiometric content of calcium carbonate in the sludge. 200 mL of 20% nitric acid (143 mL of 69.9% nitric acid diluted to 500 mL with water) was added to 100 g of the wet sludge. Taking into account water content in the sludge, the nitric acid concentration in the reaction system was 16.8% v/v. 130 mL of liquid was collected. The liquid contained 8.6% solids as was shown by evaporation of a 10-mL sample at 105° C. The theoretical concentration of calcium nitrate formed would be 8.6%. Elemental calcium content in the dried solids was 18.7±1.4 (based on three separate measurements), translating into 776% $Ca(NO_3)_2$, or 110±8% $Ca(NO_3)_2.4H_2O$.

41.4 g of the washed and dried sludge residue was collected.

EXAMPLE 36

The procedure of Example 34 was repeated, but with the difference that diluted acetic acid was used for solubilization of calcium (in the form of calcium acetate) from mixed office sludge. 150 mL of 20% acetic acid was added to 100 g of the wet sludge. Taking into account water content in the sludge, the acetic acid concentration in the reaction system was 15.9% v/v, representing 2.0 times the stoichiometric content of calcium carbonate in the sludge. 88 mL of liquid was collected. The liquid contained 10.2% solids, as was shown by evaporation of a 10-mL sample at 105° C. The theoretical concentration of calcium acetate formed would be 10.6%. Elemental calcium content in the dried solids was 21.8±0.2 (based on three separate measurements), translating into 86±1% $Ca(CH_3COO)_2$, or 96±1% $Ca(CH_3COO)_2.H_2O$.

40.3 g of the washed and dried sludge residue was collected.

EXAMPLE 37

The procedure of Example 36 was repeated, but with the difference that 200 mL of 20% acetic acid was used for solubilization of calcium, representing 2.66 times the stoichiometric content of calcium carbonate in the sludge. 200 mL of 20% acetic acid was added to 100 g of the wet sludge. Taking into account water content in the sludge, the acetic acid concentration in the reaction system was 16.8% v/v. 130 mL, of liquid was collected. The liquid contained 8.0% of solids as was shown by evaporation of a 10-mL sample at 105° C. The theoretical concentration of calcium acetate formed would be 8.3%. The elemental calcium content in the dried solids was 21.2±0.1 (based on three separate measurements), translating into 84±1% $Ca(CH_3COO)_2$, or 93±1% $Ca(CH_3COO)_2.H_2O$.

42.3 g of the washed and dried sludge residue was collected.

EXAMPLE 38

The procedure of Example 36 was repeated, but with the difference that 4.0 kg of wet mixed office sludge (48.2% moisture, calcium carbonate content of 20.4% in the dry sludge) was treated with 7.2 L of 11.6% acetic acid, representing 1.7 times the stoichiometric content of calcium carbonate content in the sludge.

The solubilization was performed as follows. 829 mL (870 g) of glacial acetic acid was mixed with 6,316 mL of tap water, making 7,145 mL of 11.6% (v/v) or 12.2% (w/w) acetic acid. This was added to 4.0 kg of the wet sludge at room temperature. Taking into account the amount of water in the sludge, the concentration of acetic acid in the resulting liquid was 9.1% (v/v) or 9.6% (w/w). The mixture was left for three days, after which supernatant was decanted, and 4.8 L of liquid was collected using a large Buchner funnel subjected to vacuum filtration using house vacuum. The pH of the liquid was 4.9. The solids content was 9.91%, as shown by evaporation of a 10-mL sample at 105° C. The theoretical amount of calcium acetate, formed in the reaction mixture, would have been 7.4% (anhydrous) or 8.2% (monohydrate) by weight. The elemental calcium content in the solids was 21.9%, translating into 86.5% calcium acetate (anhydrous), or 96.4% calcium acetate dihydrate.

EXAMPLE 39

The procedure of Example 38 was repeated, but with the difference that 5.0 kg of wet mixed office sludge (46.6% moisture, calcium carbonate content 21.1% in the dry sludge) was treated with 644 mL (676 g) of glacial acetic acid (diluted to 5.93 L with water and resulted in 10.85% acetic acid, v/v). This amount of acetic acid was stoichiometrically equivalent to the calcium carbonate in the sludge. Taking into account water content in the sludge, the acetic acid concentration in the reaction mixture liquid was 7.8% (v/v), or 8.1% (w/w).

The solubilization was performed for 4 hours at room temperature, and 5 L of liquid was collected under press. After 45 min of reaction, the elemental calcium content in a sample of the washed and dried solid residue was 2.0% (5% of calcium carbonate); after 4 hours, the solid residue contained 0.5% of elemental calcium, translating into 1.25% calcium carbonate.

Solids content in the obtained extract was 9.2%, as shown by evaporation of a 5-mL sample at 105° C. The theoretical amount of calcium acetate, formed in the reaction mixture, would have been 10.8% (anhydrous) by weight. The elemental calcium content in the solids was 22.3%, translating into 88.1% calcium acetate anhydrous, or 98.1% calcium acetate monohydrate.

When the dried solids were heated at 525° C., 44.3% of the weight loss was observed. That corresponded to the loss of one water molecule and one acetone molecule by calcium acetate (the theoretical weight loss is 43.2%). The resulting material contained 40.2% of calcium, corresponding to practically pure calcium carbonate (theoretical calcium content is 40.0%). Hence, the acetic acid extract contained practically pure calcium acetate monohydrate.

EXAMPLE 40

The procedure of Example 39 was repeated, but with a different sample of mixed office sludge (although similar in composition to the sample of Example 39), and with a smaller volume of diluted acetic acid added. The calcium carbonate content was 24.0%, and the moisture content 47.1%. 5 kg of the material was treated with 726 mL (762 g) of glacial acetic acid (diluted to 4.33 L with water, resulting in 16.8% acetic acid, v/v). This amount of acetic acid was stoichiometrically equivalent to the calcium carbonate in the sludge. Taking into account water content in the sludge, the acetic acid concentration in the reaction mixture liquid was 10.9% (v/v), or 11.3% (w/w).

The solubilization was performed for 3 hours at room temperature, and 2.9 L of liquid was collected under press. The solids content was 13.7%, as shown by evaporation of a 5-mL sample at 105° C. The theoretical amount of calcium acetate formed in the reaction mixture would have been 15% (anhydrous) by weight. Elemental calcium content in the solids was determined to be 20.4%, translating into 80.6% of calcium acetate anhydrous, or 89.8% calcium acetate monohydrate.

When the dried solids were heated at 525° C., 43.4% of the weight loss was observed. That corresponded to the loss of one water molecule and one acetone molecule by calcium acetate (the theoretical weight loss is 43.2%). The resulting material contained 39.6% of calcium, corresponding to practically pure calcium carbonate (theoretical calcium content is 40.0%). Hence, the acetic acid extract contained practically pure calcium acetate monohydrate.

EXAMPLE 41

This example describes solubilization of calcium by acetic acid (in the form of calcium acetate) from dried mixed office sludge. The initial sludge material was dried, dust-free, not screened, and had a moisture content of 3.9%, an ash content 60%, and an elemental calcium content of 5.4%, resulting in a calcium carbonate content of 13.5% in the whole dried sludge.

The solubilization was performed as follows. 300 g of the dried sludge was added by portions of 80–120 g into 625 mL of 20% acetic acid (prepared by mixing 125 mL of glacial acetic acid and 500 mL of tap water) at room temperature. The acetic acid concentration in the reaction system was 2.6 times the stoichiometric proportion of calcium carbonate in the sludge. A moderate evolution of carbon dioxide was observed. The mixture was left overnight, following which supernatant was decanted, and 310 mL of the brownish liquid was then collected. The solids content was 15.7%, as was shown by evaporation of a 10-mL sample at 105° C. The elemental calcium content in the liquid was 28,250 ppm, translating into 11.2% calcium acetate.

Complete solubilization of calcium carbonate (13.5% in the sludge, as noted above, or 40.5 g in 300 g of the sludge) would theoretically yield 64 g of calcium acetate in 625 mL total solution, i.e., 10.2%. This figure can be compared with the 11.2% concentration of calcium acetate determined experimentally.

The washed and dried sludge residue (after the acid extraction) included 49% ash, compared with 60% ash content in the initial sludge material.

EXAMPLE 42

The procedure of Example 41 was repeated, but with the difference that 3.84 kg of the dried sludge was added by batches of 100–200 g into 8 L of 20% acetic acid (prepared by mixing of 1.6 L of glacial acetic acid and 6.4 L of tap water). The acetic acid concentration in the reaction system was 2.6 times the stoichiometric proportion of calcium carbonate in the sludge. After overnight incubation the supernatant was decanted, and the collected insoluble sludge residue placed into a large Buchner funnel and subjected to vacuum filtration using house vacuum. 3.9 L total of the liquid, pH 4.4, was collected. The liquid was filtered through Whatman No. 1 filter paper, resulting in a brownish clear solution with solids content of 15.4% (shown by evaporation of a 10-mL sample at 105° C.). The calcium content in the liquid was 23,000 ppm, translating into 9.1% calcium acetate.

Complete solubilization of calcium carbonate (13.5% in the sludge, see Example 41, or 518.4 g in 3.84 kg of the sludge) would theoretically yield 819.07 g of calcium acetate in 8 L of total solution, that is 10.2%. This figure can be compared to the 9.1% concentration of calcium acetate determined experimentally.

EXAMPLE 43

The procedure of Example 41 was repeated, but with the difference that another, high-ash sludge material was treated with 20% acetic acid. The sludge material was dried, dust-containing, with a moisture content of 5%, an ash content of 63%, and an elemental calcium content of 17.2%, translating into a calcium carbonate content of 43%.

171.2 g of the dried sludge was added carefully into 625 mL of 20% acetic acid (prepared by mixing of 125 mL of glacial acetic acid and 500 mL of tap water) at room temperature. The acetic acid concentration in the reaction system was 1.5 times the stoichiometric proportion of calcium carbonate in the sludge. A violent evolution of carbon dioxide was observed, forming a thick "beer head." The mixture was left overnight to ensure completion of the reaction. Supernatant was then separated by a multiple stepwise decanting, since the dusty, insoluble sludge residue did not allow a clean direct decanting. 300 mL of turbid liquid was collected over a 24-hr period. After filtration, the solids content in the liquid was observed to be 18.7%, as shown by evaporation of a 10-mL sample at 105° C.

Complete solubilization of calcium carbonate in the sludge (73.6 g in 171.2 g of the sludge) would theoretically yield 116.3 g of calcium acetate in 625 mL of total solution, i.e., 18.6%, practically identical to the 18.7% concentration of solids determined experimentally.

EXAMPLE 44

This example describes solubilization of calcium (in the form of calcium chloride) from yet another mixed office sludge, combusted under controlled conditions, namely at 525° C. The dry ash contained 24.9% elemental calcium, translating into 62.3% calcium carbonate. The solubilization was performed by diluted HCl, in amount of 1.3 times the stoichiometric proportion of calcium carbonate content.

The solubilization was performed as follows. 500 mL of 11.9% (w/w) of HCl, prepared by diluting 535 mL (636.65 g) of 37.4% HCl to 2 L, was added to 100 g of the dry ash. That amount of HCl was 31% higher than the stoichiometric amount needed for a complete solubilization of the calcium carbonate present in the ash. The mixture was agitated and left overnight at room temperature. Supernatant was then separated from the solid residue by decanting and filtering, and 243 mL of liquid was collected. The liquid contained 15.8% of solids, as was shown by evaporation of a 10-mL sample at 105° C. The elemental calcium content in the dried solids was 27.6%, translating into 77% CaCl, or 101% $CaCl_2.2H_2O$.

Combustion of the dried solids at 525° C. reduced their weight by 24.7% (the theoretical value for transition of $CaCl_2.2H_2O$ into $CaCl_2$ is 24.5%), and the elemental calcium content in the combusted solids was 29%, translating into 80% $CaCl_2$ in the total solids. 48.5 g of the washed and dried sludge residue was collected. Elemental calcium content in the residue was determined to be 3.3%. The material contained primarily clay.

EXAMPLE 45

The procedure of Example 44 was repeated, but with the difference that the ash, treated with diluted HCl, was obtained by combustion at 900° C. The dry ash contained 30.0±0.4% elemental calcium, translating into 42.0±0.6% calcium oxide equivalent. The amount of HCl, used for the solubilization, was 1.09 times the stoichiometric proportion of calcium carbonate in the ash.

The solubilization was performed as follows. 170 mL of 11.9% (w/w) HCl, prepared as described in Example 44, was added to 34 g of the dry ash. That amount of HCl was 9% higher compared with the stoichiometric amount needed for complete solubilization of calcium carbonate present in the ash. The mixture was agitated and left overnight at room temperature. Supernatant was then separated from the solid residue by decanting and filtering, and 72 mL of liquid was collected. The liquid contained 18.8% solids, as shown by evaporation of a 10-mL sample at 105° C. Elemental calcium content in the dried solids was 27.4%, translating into 76% CaCl, or 100% $CaCl_2.2H_2O$.

Combustion of the dried solids at 525° C. reduced their weight by 25.5% (the theoretical value for transition of $CaCl_2.2H_2O$ into $CaCl_2$ is 24.5%), and the elemental calcium content in the combusted solids was 32.3%, translating into 90% $CaCl_2$ in the total solids. 24 g of the washed and dried sludge residue was collected. Elemental calcium content in the residue was determined to be 7.8%.

EXAMPLES 46 AND 47

The procedure of Example 44 was repeated, but with the difference that diluted nitric acid was used for solubilization of calcium (in the form of calcium nitrate) from the ash obtained by combustion of the mixed office sludge at 525° C. 200 g of the ash was mixed with 1.8 L of 20% nitric acid, prepared as in Example 35. That amount of nitric acid corresponded to 2.3 times the stoichiometric proportion of calcium carbonate in the ash. The slurry was agitated and left overnight at room temperature. The liquid collected was of a gel-like appearance and contained 18.5% of solids, as shown by evaporation of a 10-mL sample at 105° C. The elemental calcium content in the dried solids was 13.75±0.05% (based on two independent measurements), translating into 56.4% $Ca(NO_3)_2$, or 81.2% $Ca(NO_3)_2.4H_2O$.

In a similar experiment, 200 g of the ash was mixed with 3.0 L of 20% nitric acid, prepared as in Example 35. That amount of nitric acid corresponded to 3.8 times the stoichiometric proportion of calcium carbonate in the ash. The slurry was agitated and left overnight at room temperature. The liquid collected contained 11.0±0.1% of solids (based on two separate measurements), as was shown by evaporation of a 10-mL sample at 105° C. The elemental calcium content in the dried solids was 13.6±0.1% (based on two independent measurements), translating into 55.8% $Ca(NO_3)_2$, or 80.3% $Ca(NO_3)_2.4H_2O$.

Combustion of the dried solids from both experiments at 525° C. reduced their weight by 64% (the theoretical value for the transition of $Ca(NO_3)_2.4H_2O$ into anhydrous calcium carbonate is 57.6%). The calcium content in the combusted solids was determined to be 38.4%, corresponding to calcium carbonate of 96% purity.

EXAMPLES 48 AND 49

The procedure of Examples 46–47 was repeated, but with the difference that diluted acetic acid was used for solubilization of calcium (in the form of calcium acetate) from the ash obtained by combustion of the mixed office sludge at 525° C. 200 g of the ash was mixed with 1.8 L of 20% (v/v) or 21% (w/w) acetic acid. That amount of acetic acid corresponded to 2.5 times the stoichiometric proportion of calcium carbonate in the ash. The slurry was agitated and left overnight at room temperature. The liquid collected contained 14.0% solids, as shown by evaporation of a 10-mL sample at 105° C. The theoretical amount of calcium acetate, formed in the reaction mixture, would have been 10.9% solids. The elemental calcium content in the dried solids was determined to be 19.6±0.8% (based on four independent measurements), translating into 77% $Ca(CH_3COO)_2$, or 86% $Ca(CH_3COO)_2.H_2O$.

In a similar experiment, 200 g of the ash was mixed with 3.0 L of 20% (v/v) or 21% (w/w) acetic acid. That amount of acetic acid corresponded to 4.2 times the stoichiometric proportion of calcium carbonate in the ash. The slurry was agitated and left overnight at room temperature. 2.7 L of liquid was collected. The liquid collected contained 9.2±0.2% solids (based on two separate measurements), as was shown by evaporation of a 10-mL sample at 105° C. The theoretical amount of calcium acetate, formed in the reaction mixture, would have been 6.6% by weight. The elemental calcium content in the dried solids was determined to be 19.2±0.4% (based on two independent measurements), translating into 76% $Ca(CH_3COO)_2$, or 85% $Ca(CH_3COO)_2.H_2O$.

Combustion of the dried solids from both experiments at 525° C. reduced their weight by 53% (the theoretical value for the transition of $Ca(CH_3COO)_2.H_2O$ into anhydrous calcium carbonate is 43.2%, see Examples 39 and 40). The calcium content in the combusted solids was determined to be 39.2%, corresponding to 98% calcium carbonate. Since the initial ash did not contain organic matter, the last figure indicates that the acetic acid extract contained calcium acetate of 98% purity.

EXAMPLES 50 THROUGH 57

These examples describe and compare solubilization of calcium (in the form of calcium nitrate or calcium acetate) from mixed office sludge, combusted under controlled conditions, namely, at 525° C., 800° C., 900° C., and 1000° C. The dry ash contained 24.9% elemental calcium, translating into 62.3% calcium carbonate or 34.9% calcium oxide equivalent. The solubilization was performed by treating of 1 g of the dry ash with 15 mL of 20% nitric acid or 20% acetic acid, in amounts corresponding to 3.8 and 4.0, respectively, times the stoichiometric proportion of calcium carbonate or calcium oxide equivalent (for calcined ash samples) in the sludge. The theoretical concentrations of $Ca(NO_3)_2$ and $Ca(NO_3)_2.4H_2O$, $Ca(CH_3COO)_2$ and $Ca(CH_3COO)_2.H_2O$ formed are, respectively, 6.8% and 9.8%, 6.6% and 7.3%.

The following table shows the experimental results in terms of the amount of solids extracted from the ash after the liquids collected were dried at 105° C. The average volume of the liquids collected was 12.0±1.3 mL for nitric acid solubilization, and 11.2±1.2 mL for acetic acid solubilization.

TABLE 11

Concentration of solids extracted from ash obtained by combustion of mixed office sludge. 1 g of ash was treated with 15 mL of 20% acid in each experiment. Theoretical concentrations for the given experimental conditions: $Ca(NO_3)_2$-6.8%, $Ca(NO_3)_2 \cdot 4H_2O$ -9.8%, $Ca(CH_3COO)_2$-6.6%, $Ca(CH_3COO)_2 \cdot H_2O$-7.3%

| Combustion temperature, | Solids concentration in the extracts collected, % | |
|---|---|---|
| degrees Celcius | 20% Nitric acid | 20% Acetic acid |
| 525 | 9.3 ± 0.4 | 6.9 ± 0.1 |
| 800 | 12.6 ± 0.6 | 10.4 |
| 900 | 12.9 | 11.2 |
| 1000 | 8.1 | 8.8 |

The treatment of calcined ash (at 800, 900, and 1000° C.) with both 20% nitric acid and 20% acetic acid resulted in formation of a yellow slimy gel-like mass that is rather difficult to separate from the extract.

EXAMPLES 58 THROUGH 60

These examples describe and compare the solubilization of calcium (in the form of calcium chloride, calcium nitrate or calcium acetate) from an industrial incineration ash. The moisture content in the ash was 32.3%. The dried ash contained 16.5% elemental calcium, translating into 23.1% calcium oxide equivalent.

The solubilization was performed as in Example 44, but with the difference that hydrochloric, nitric, and acetic acids were used, and in amounts close to the stoichiometric equivalent of the calcium oxide in the ash. 100 g of dry incineration ash was treated with the following acid solutions:

(Example 58) 300 mL of 8.67% HCl, prepared by diluting of 225 mL (267.75 g) of 37.4% HCl to 500 mL with water, resulting in 20% w/w HCl, and by a further mixing of 130 mL of the 20% acid with 170 mL of water;

(Example 59) 400 mL of 13% nitric acid, prepared by diluting of 143 mL of 69.9% nitric acid to 500 mL with water, resulting in 20% $HNO_3$, and by a further mixing of 260 mL of 20% nitric acid with 140 mL of water; and (Example 60) 400 mL of 13.1% acetic acid, prepared by diluting of 125 mL of glacial acetic acid to 625 mL with water, resulting in 21% (w/w) acetic acid, and by a further mixing of 250 mL of 21% nitric acid with 150 mL of water.

In all the three examples the amounts of the acids were close to stoichiometric equivalents: 3% excess of the acid, no excess, and 6% excess, respectively. The amount of extract recovered was 200 mL (Example 58), 210 mL (Example 59) and 270 mL (Example 60). The theoretical amount of solids (as anhydrous salts) in the extracts were: 15.3% for $CaCl_2$, 16.9% for $Ca(NO_3)_2$, and 16.3% for $Ca(CH_3COO)_2$.

Table 12 shows experimental results in terms of amount of solids extracted from the ash, after the liquids collected were dried at 105° C.

TABLE 12

Concentration of solids extracted from an industrial incineration ash. 100 g of ash was treated with approximately stoichiometric amounts of hydrochloric, nitric, and acetic acids. Theoretical concentrations for the given experimental conditions: $CaCl_2$-15.3% (Ca content 36.0%), $CaCl_2 \cdot 2H_2O$-20.2% (Ca content 27.2%), $Ca(NO_3)_2$-16.9% (Ca content 24.4%), $Ca(NO_3)_2 \cdot 4H_2O$-24.4% (Ca content 16.9%), $Ca(CH_3COO)_2$-16.3% (Ca content 25.3%), $Ca(CH_3COO)_2 \cdot H_2O$-18.1% (Ca content 22.7%)

| Acid | Solids concentration in the extracts, dried at 105° C. % | Ca content in solids, dried at 105° C., % | Weight loss of solids at 525 °C., % | Ca content in combusted solids, % |
|---|---|---|---|---|
| Hydrochloric | 11.9 ± 1.3 | 25.2 | 21.5 | 33.1 |
| Nitric | 23.7 ± 0.5 | 21.7 | 52.4 | 40.3 |
| Acetic | 10.5 ± 1.1 | 25.7 | 46.7 | 36.1 |

It is apparent that acid-extracted chlorides, nitrates, and acetates, dried at 105° C., contained a high fraction of components, volatile at 525° C. and/or decomposed at that temperature. In the case of calcium chloride, combustion eliminates bound water. Calcium nitrate converts to practically pure calcium carbonate (the theoretical calcium content is 40%, compared to 40.3% in Table 12). Calcium acetate loses a water molecule and an acetone molecule (the theoretical weight loss is 42.3%) and converts to calcium carbonate (the theoretical calcium content is 40%, compared to 36.1% in Table 12, corresponds to $CaCO_3$ of 90.3% purity).

EXAMPLES 61 THROUGH 63

This example describes precipitation of calcium carbonate from calcium chloride solutions obtained by processing of the mixed office sludge (Example 25), and ash residues after combustion of the sludge at 525° C. (Example 44) and 900° C. (Example 45).

The precipitation was performed by adding solutions of potassium carbonate, potassium bicarbonate, or sodium carbonate either to the calcium chloride solutions directly, or to the calcium chloride solutions diluted 4- to 20-fold. The addition of potassium carbonate to the calcium chloride solutions (with no dilution) caused an almost immediate hardening of the solution due to the instant formation of calcium carbonate. When the calcium chloride solution is diluted 20-fold, addition of 1–5% v/v of the potassium carbonate solution leads to a fast formation of flakes of precipitated calcium carbonate. Microphotographs showed that the precipitated calcium carbonate formed right spheres of 1–2 microns in diameter (for some particular cases), with the size and shape of particles depending upon precipitation conditions.

Table 13 shows the results of precipitating calcium carbonate by adding potassium carbonate (0.67 mg/mL) into the calcium chloride solutions. 10 mL each of the calcium-containing extracts, obtained in Examples 25, 44, and 45, were diluted to 40 mL, 3 mL of the potassium carbonate solution was added, precipitate was collected by centrifugation, dried at 105° C. and weighed, and elemental calcium content was determined. The supernatant was mixed with another 3 mL of potassium carbonate solution, and the precipitate was collected, dried, and analyzed as described above. In a separate experiment, 12 mL of potassium carbonate was added into 40 mL of diluted calcium-containing extract, as described above.

TABLE 13

Precipitation of calcium-containing carbonates from calcium chloride-containing extracts obtained from mixed office sludge and calcined sludge (Examples 25, 44, 45)

| Initial material | $K_2CO_3$ added, mL | Precipitate, at 105° C. | | | Precipitate, at 525° C. | | |
|---|---|---|---|---|---|---|---|
| | | Carbonates, mg | Ca, % | $CaCO_3$ % | Weight loss, % | Ca, % | $CaCO_3$ % |
| Sludge | 3 | 264 | 35.0 | 88 | 7.8±0.2 | 37.7 | 94 |
| | +3 | 289 | 34.7 | 87 | 5.1±0.8 | 36.5 | 91 |
| | 12 | 1,261 | 35.3 | 88 | 5.5 | 37.4 | 94 |
| Ash, 525 °C. | 3 | 661 | 32.8 | 82 | 6.1 | 32.4 | 81 |
| | +3 | 542 | 37.2 | 93 | 4.2 | 37.3 | 93 |
| | 12 | 1,359 | 33.7 | 84 | 6.6 | 34.7 | 87 |
| Ash, 900 °C. | 3 | 901 | 38.4 | 96 | 1.5 | 38.0 | 95 |
| | +3 | 767 | 38.0 | 95 | 1.0 | 38.1 | 95 |
| | 12 | 1,913 | 33.4 | 84 | 8.0 | 35.8 | 90 |

The data show that the calcium carbonate content in the dried precipitate before and after its combustion at 525° C. was 88±1% and 93±2%, respectively (from sludge), 86±6% and 87±6% (from ash at 525° C.), and 92±7% and 93±3% (from ash at 900° C.). It is apparent that the precipitated calcium carbonate does not contain bound water, and its purity is in the neighborhood of 93%.

EXAMPLE 64

The procedure of Examples 61–63 was repeated, but with the difference that calcium carbonate was precipitated from the combined calcium nitrate solutions obtained in Examples 46 and 47. The mixed office sludge, combusted at 525° C., was used as the source of calcium, as described in those Examples.

Table 14 shows the results of precipitating calcium carbonate by adding potassium carbonate (0.67 mg/mL) into the calcium nitrate solution. 10 mL of the calcium-containing extract was diluted to 40 mL, 3 mL of the potassium carbonate solution was added, precipitate was collected by centrifugation, dried at 105° C. and weighed, and the elemental calcium content was determined. The supernatant was mixed with another 3 mL of potassium carbonate solution, and the precipitate was collected, dried, and analyzed as described above. The second supernatant was mixed with 4 mL of potassium carbonate solution, and the precipitate was collected, dried, and analyzed as described above.

TABLE 14

Precipitation of calcium-containing carbonates from calcium nitrate-containing extracts obtained from mixed office sludge combusted at 525° C. (Examples 46–47)

| $K_2CO_3$ added, mL | Precipitate, at 105° C. | | Precipitate, at 525° C. | |
|---|---|---|---|---|
| | Ca, % | $CaCO_3$ % | Ca, % | $CaCO_3$ % |
| 3 | 25.2 | 63 | n.d. | n.d. |
| +3 | 23.8 | 60 | 33.2 | 83 |
| +4 | 27.7 | 69 | 35.2 | 88 |

EXAMPLE 65

The procedure of Example 64 was repeated, but with the difference that calcium carbonate was precipitated from combined calcium acetate solutions, obtained in Examples 48 and 49. The mixed office sludge, combusted at 525° C., was used as the source of calcium, as described in those Examples. The data are shown in the following Table 15.

TABLE 15

Precipitation of calcium-containing carbonates from calcium acetate-containing extracts obtained from mixed office sludge combusted at 525° C. (Examples 48–49)

| $K_2CO_3$ added, mL | Precipitate, at 105° C. | | | Precipitate, at 525° C. | | |
|---|---|---|---|---|---|---|
| | Carbonates, mg | Ca, % | $CaCO_3$ % | Weight loss, % | Ca, % | $CaCO_3$ % |
| 3 | 100 | 25.5 | 64 | n.d. | 28.8 | 72 |
| +3 | 113 | 28.8 | 72 | 20.4 | 39.0 | 98 |
| +4 | 145 | 35.5 | 89 | 8.3 | 39.2 | 98 |

EXAMPLE 66

The procedure of Examples 61–63 was repeated, but with the difference that calcium carbonate was precipitated from the calcium chloride, calcium nitrate, and calcium acetate solutions, obtained in Examples 58 through 60. The industrial incineration ash was used as the source of calcium, as described in those Examples. The data are shown in the following Table 16.

TABLE 16

Precipitation of calcium-containing carbonates from calcium chloride-, calcium nitrate-, and calcium acetate-containing extracts obtained from industrial incineration ash (Examples 58–60)

| Acid | $K_2CO_3$ added, mL | Precipitate, at 105° C. | | | Precipitate, at 525° C. | | |
|---|---|---|---|---|---|---|---|
| | | Carbonates, mg | Ca, % | $CaCO_3$ % | Weight loss | Ca, % | $CaCO_3$ % |
| HCl | 3 | little | n.d. | n.d. | n.d. | n.d. | n.d. |
| | +3 | 875 | 33.7 | 84 | 7.6 | 36.3 | 91 |
| | 12 | 932 | 36.4 | 91 | 7.1 | 38.2 | 98 |
| $HNO_3$ | 3 | 457 | n.d. | n.d. | n.d. | n.d. | n.d. |
| | +3 | 805 | 23.4 | 59 | 18.7 | 25.7 | 64 |
| | 12 | 1,407 | 24.0 | 60 | 17.3 | 29.0 | 73 |
| $CH_3COOH$ | 3 | 473 | 25.8 | 65 | 15.4 | 31.3 | 78 |
| | +3 | 107 | 28.2 | 71 | n.d. | n.d. | n.d. |
| | 12 | 702 | 26.5 | 66 | 12.5 | 31.1 | 78 |

It is apparent that the purest calcium carbonate was obtained from calcium chloride (up to 98% purity in the combusted material), followed by that obtained from calcium acetate (78% purity), and by that obtained from calcium nitrate (up to 73% purity).

It is also apparent that carbonates precipitated from nitrates and acetates contained significantly more combustible (at 525° C.) components compared to carbonates precipitated from chlorides. Among those combustible components can be bound water, carbonates of some other elements, etc.

EXAMPLE 67

The procedure of Example 41 was repeated, but with the difference that after decanting of the obtained calcium acetate solution, residual insoluble sludge granules, impregnated with calcium acetate acidic solution, were collected, air-dried, and tested as a de-icer by means of a direct application onto ice. Ice cubes were taken from −20° C. freezer, crushed in a blender, put into two identical 15-cm Petri dishes, and kept at −20° C. for an hour to make the ice crush rock-solid. Then ice in one dish was covered with granules impregnated with calcium acetate, and both dishes (test and control) were placed in a freezer at −6° C. Soon ice in the test dish started to release water, while ice in the control dish remained solid (no water was released).

It is apparent that granules impregnated with calcium acetate show distinct de-icing properties.

It will be apparent from the above that a new and unique process has been disclosed for the recovery of calcium salts from papermaking sludge. These salts are suitable for many uses, including preparation of reagent chemicals, such as calcium chloride, calcium nitrate, calcium acetate, and so forth, precipitation as calcium carbonate, preparation of liquid and solid de-icers, such as calcium acetate alone and in combination with known de-icing chemicals such as magnesium salts, preparation of sulfur-capturing sorbents based on calcium salts, etc. This process therefore provides new use for calcium-containing paper sludges that heretofore have primarily been burned or landfilled, creating environmental pressure. It will be clear from the present disclosure that calcium salts resulting from waste paper sludge in general may be utilized for a wide variety of purposes.

Although this invention has been described in its preferred form and preferred practice with a certain degree of particularity, it is understood that the present disclosure of the preferred form and preferred practice has been made only by way of example and that numerous changes may be resorted to without departing from the spirit and the scope of the invention as hereinafter claimed.

What is claimed is:

1. A method of extracting calcium from an aqueous mixture comprising papermaking sludge, the mixture comprising solid and liquid phases, the method comprising the steps of:
   a. combining the mixture with an acid to solubilize substantially all calcium present in the mixture;
   b. incubating the mixture;
   c. without precipitating calcium, separating a calcium-containing liquid fraction; and
   d. recovering calcium salt from the liquid fraction.

2. The method of claim 1 wherein the acid is selected from the group consisting of hydrochloric acid, nitric acid, acetic acid, and phosphoric acid.

3. The method of claim 1 wherein the mixture is combined with an amount of acid ranging from 0.1% to 35% by weight.

4. The method of claim 3 wherein the mixture is combined with an amount of hydrochloric acid ranging from 2% to 20% by weight.

5. The method of claim 4 wherein the mixture is combined with 3% to 6% of hydrochloric acid by weight.

6. The method of claim 2 wherein the mixture contains an amount of calcium carbonate, the acid being present in a molar ratio ranging from 0.8 to 1.5 relative to the calcium carbonate.

7. The method of claim 3 wherein the mixture is combined with an amount of nitric acid ranging from 2% to 25% by weight.

8. The method of claim 7 wherein the amount of nitric acid is 8% by weight.

9. The method of claim 3 wherein the mixture is combined with an amount of acetic acid ranging from 2% to 30% by weight.

10. The method of claim 9 wherein the mixture is combined with 8% of acetic acid by weight.

11. The method of claim 2 wherein the mixture contains an amount of calcium carbonate, the acid being nitric acid present in a molar ratio ranging from 0.8 to 2.0 relative to the calcium carbonate.

12. The method of claim 1 wherein the sludge is derived from at least one of (a) fine paper sludge, (b) coated paper sludge, (c) coated fine paper sludge, (d) coated groundwood paper sludge, (e) recycle mixed office paper sludge, (f) recycled newsprint, (g) de-inked paper mill sludge.

13. The method of claim 1 wherein the recovering step comprises carbonating the mixture to precipitate calcium salts.

14. The method of claim 1 wherein the separating step comprises at least one of (a) filtration, (b) centrifugation, and (c) dewatering of residual plant fiber.

15. A method of extracting calcium from an aqueous mixture comprising ash derived from papermaking sludge, the mixture comprising solid and liquid phases, the method comprising the steps of:
   a. combining the mixture with an acid to solubilize substantially all calcium present in the mixture;
   b. incubating the mixture;
   c. without precipitating calcium, separating a calcium-containing, solids-free liquid fraction; and
   d. recovering calcium salts from the liquid fraction.

16. The method of claim 15 wherein the acid is selected from the group consisting of hydrochloric acid, nitric acid, acetic acid, and phosphoric acid.

17. The method of claim 15 wherein the mixture is combined with an amount of acid ranging from 2% to 35% by weight.

18. The method of claim 17 wherein the mixture is combined with an amount of hydrochloric acid ranging from 5% to 25% by weight.

19. The method of claim 18 wherein the mixture is combined with 8% to 14% of hydrochloric acid by weight.

20. The method of claim 16 wherein the mixture contains an amount of calcium carbonate, the acid being present in a molar ratio ranging from 0.8 to 1.5 relative to the calcium carbonate.

21. The method of claim 17 wherein the mixture is combined with an amount of nitric acid ranging from 5% to 20% by weight.

22. The method of claim 21 wherein the amount of nitric acid is 8% to 10% by weight.

23. The method of claim 17 wherein the mixture is combined with an amount of acetic acid ranging from 5 to 20% by weight.

24. The method of claim 23 wherein the mixture is combined with 10% to 13% of acetic acid by weight.

25. The method of claim 16 wherein the mixture contains an amount of calcium carbonate, the acid being acetic acid present in a molar ratio ranging from 0.8 to 2.0 relative to the calcium carbonate.

26. The method of claim 15 wherein the recovering step comprises carbonating the mixture to precipitate calcium salts.

27. The method of claim 15 wherein the separating step comprises at least one of (a) filtration, (b) centrifugation, and (c) dewatering of residual plant fiber.

* * * * *